United States Patent [19]

Barrett

[11] 3,954,869

[45] May 4, 1976

[54] 1-(HALO-BIPHENYL)-1-(HALO-PHENYL)-3-AMINOPROP-1-ENES AND THE SALTS THEREOF

[75] Inventor: Paul Anthony Barrett, Beckenham, England

[73] Assignee: Burroughs Wellcome Co., Research Triangle Park, N.C.

[22] Filed: Mar. 27, 1974

[21] Appl. No.: 455,386

[30] Foreign Application Priority Data

Mar. 28, 1973 United Kingdom............... 14893/73

[52] U.S. Cl. ...................... 260/570 R; 260/348 R; 260/456 P; 260/465 F; 260/465 K; 260/488 CD; 260/501.1; 260/551 R; 260/558 R; 260/562 P; 260/568; 260/570.5 C; 260/583 E; 260/618 R; 260/646; 424/316; 424/33 D

[51] Int. Cl.².......................................... C07C 87/29

[58] Field of Search ...................... 260/501.1, 570 R

[56] References Cited

UNITED STATES PATENTS

| | | | |
|---|---|---|---|
| 2,532,292 | 12/1950 | Cusic .................................. | 260/570 |
| 3,250,767 | 5/1966 | Benczr ............................. | 260/570 X |
| 3,375,278 | 3/1968 | Moffett .............................. | 260/570 |

FOREIGN PATENTS OR APPLICATIONS 1,134,715    11/1968    United Kingdom................ 260/570

OTHER PUBLICATIONS

White et al., "Brit. J. Pharmacol.," Vol. 6, pp. 560–571 (1951).

Primary Examiner—Robert V. Hines
Attorney, Agent, or Firm—Donald Brown

[57] ABSTRACT

Novel substituted 3-aminoprop-1-enes of formula (I)

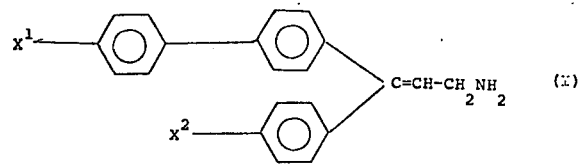

wherein $X^1$ and $X^2$ are the same or different and each may represent a halogen atom, methods of preparing them and pharmaceutical formulations containing them.

The above compounds have activity against infections of *Trypanosoma cruzi*.

24 Claims, No Drawings

1-(HALO-BIPHENYL)-1-(HALO-PHENYL)-3-AMINOPROP-1-ENES AND THE SALTS THEREOF

This invention relates to novel substituted 3-aminoprop-1-enes, to methods of preparing the 3-aminoprop-1-enes and to pharmaceutical formulations containing the same.

Infections by the organism *Trypanosoma cruzi* are fairly common in South Africa and cause Chagas' disease in humans. This disease has heretofore proved to be extremely difficult to treat.

One drug which has been used in the treatment of the disease is 4-(5-nitrofurfurylidene)amino)-3-methylthiomorpholine-1,1-dioxide known by the Trade Name "Lampit". Unfortunately this drug, whilst having some activity against the trypanosomes, is fairly toxic and therefore may be unsuitable for use in human treatment at high dosage levels.

According to the present invention there is provided a substituted 3-amino-prop-1-ene of formula (I),

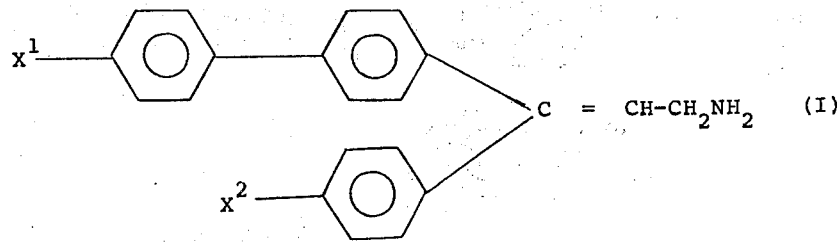

wherein $X^1$ and $X^2$ are the same or different and may each represent a halogen atom, or a salt thereof, especially a pharmaceutically acceptable salt thereof. Such compounds have surprising activity against infections of *T. cruzi*.

These compounds of formula (I) exhibit geometrical isomerism and can be separated into their cis and trans isomers. Although the trans isomers may have good activity, in general the cis isomers, i.e. those in which the parahalo biphenylyl and $CH_2NH_2$ groups are in a cis relationship, have the higher activity and are hence preferred.

The following compounds of formula (I), as a mixture or as their separated geometrical isomers, are preferred:

1-(4'-chloro-4-biphenylyl)-1-p-chlorophenyl-3-aminoprop-1-ene;
1-(4'-bromo-4-biphenyl)-1-p-chlorophenyl-3-aminoprop-1-ene;
1-(4'-bromo-4-biphenylyl)-1-p-bromophenyl-3-aminoprop-1-ene.

In a further aspect of the present invention there is provided a method of preparing a compound of formula (I) as described above which comprises A. reacting a compound of formula (V)

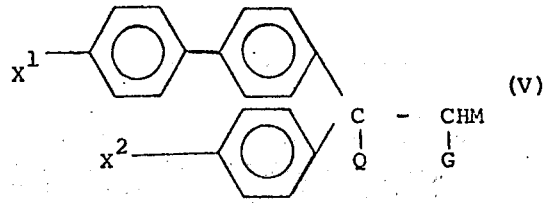

where $X^1$ and $X^2$ are as defined above, as specified hereunder;

a. when Q and G taken together represent a single bond,
 i. when M represents a nitrile group; or a group of formula $CYNH_2$ where Y is an oxygen or sulphur atom; selectively reducing the compound so that the double bond in the C = C moiety remains unreduced;
 ii. when M represents a group of formula $CH_2Z$, where Z represents a readily displaceable group such as a bromo or tosyloxy group, re-

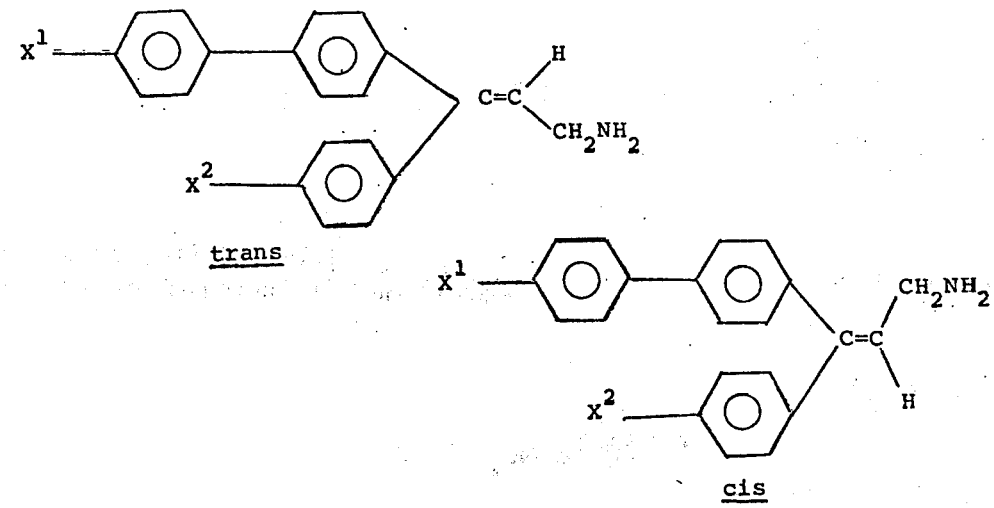

acting the compound of formula (V) with ammonia; or iii. when M represents a group of formula CH$_2$NHB where B is a protecting group, such as an acyl group, removing the protecting group;

b. or when Q represents a nucleophilic group, for example a hydroxy, chloro, bromo, iodo, acyloxy, sulphonyloxy, amino or substituted amino group, G represents a hydrogen atom and M represents a group of formula CH$_2$NH$_2$ eliminating a molecule of GQ from a molecule of formula (V); or B. reacting a phosphorane of formula (VI)

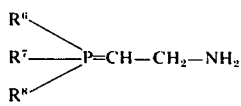

wherein R$^6$, R$^7$ and R$^8$ are alkyl or phenyl groups, with a ketone of formula (VII)

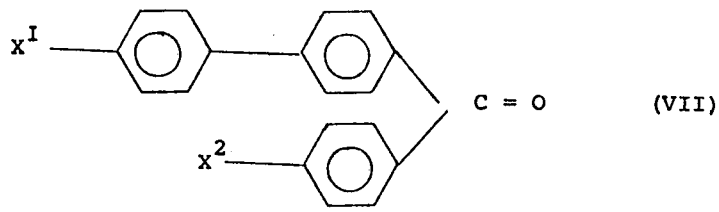

or

C. reducing a compound of formula (VIII)

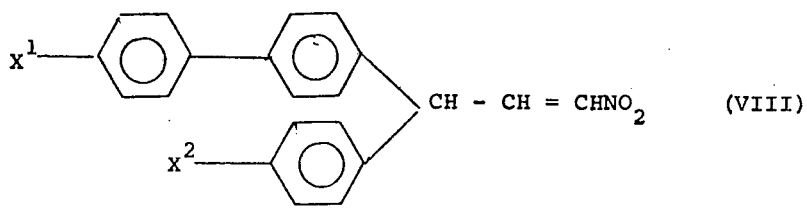

To prepare the preferred cis isomer of a compound of formula (I), as defined above, the method comprises the additional step of separating this cis-isomer from the trans-isomer.

In the case where M represents a nitrile group and Q and G represent a single bond, the compound of formula (V) has the structure (IX) (c.f. method (A) (a) (i))

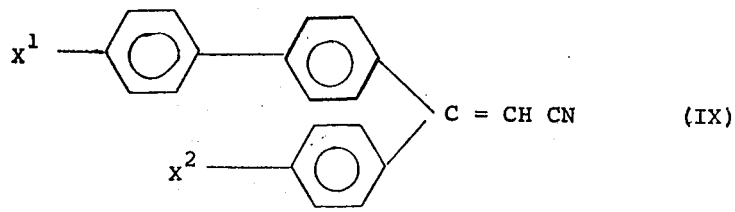

Reduction of this compound can be carried out using the process described by Jones and Maisey in *J. Med. Chem.* 1971, 14, 161.

When M represents the group CYNH$_2$ and Q and G represent a single bond the compound of formula (V) has the structure (X) (c.f. method (A) (a) (i))

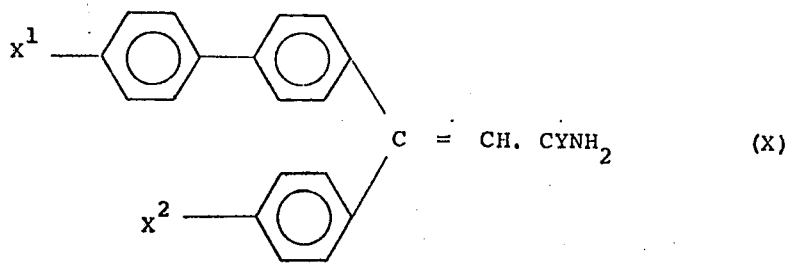

When Y is an oxygen atom, (X) then being an amide, reduction may be carried out, for example, by means of a metallic hydride, such as sodium borohydride, lithium aluminium hydride, or by diborane. When Y is a sulphur atom, reduction may be carried out, for example, by means of a Raney nickel catalyst. The amides can be prepared using a procedure similar to that outlined in *Chemical Abstracts* 65, 615 g. 1966. The corresponding sulphur compounds can be prepared by reacting the

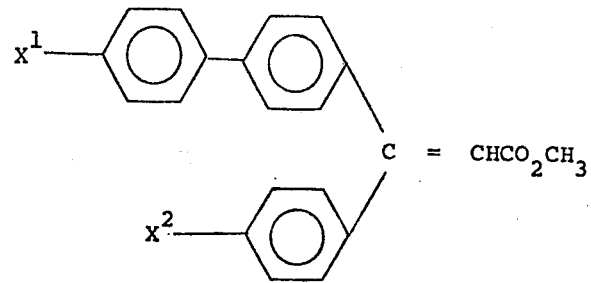

appropriate nitrile with hydrogen sulphide in ethanol under pressure or by reacting the corresponding amide with $P_2S_5$.

When M represents a group of formula $CH_2Z$ and Q and G represent a single bond the compound of formula (V) has the structure (XIII) (c.f. method (A) (a) (ii))

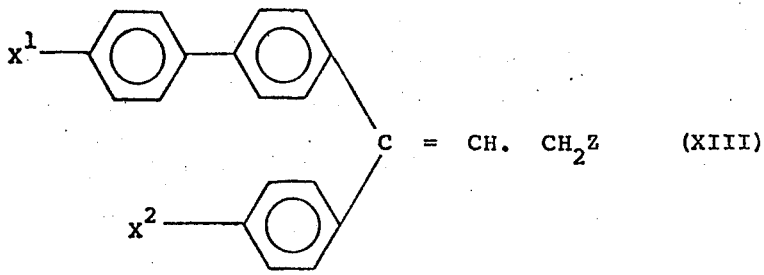

which can itself be prepared by a Wittig reaction between a ketone of formula (VII) and diethylphosphonoacetate.

When M represents a group of formula $CH_2NHB$ and Q and G represent a single bond the compound of formula (V) can be represented by the formula (XIV) (c.f. method (A) (a) (iii))

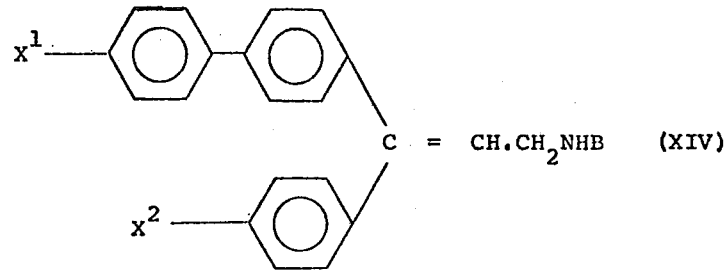

Compounds where Z represents a bromine atom can be prepared from the corresponding prop-1-ene using N - bromo succinimide and azobisisobutyronitrile. Compounds where Z represents a tosyloxy group can be prepared from the corresponding alcohol using p-toluene sulphonyl chloride. This alcohol, which has the structure

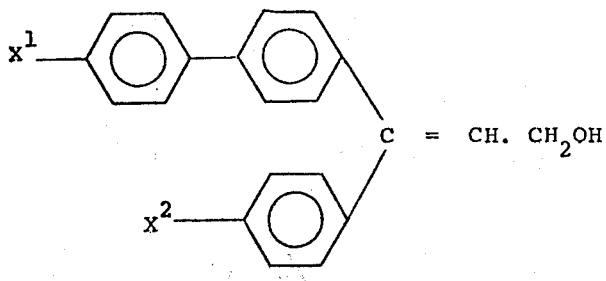

can be prepared by the reduction of the $\alpha, \beta$ - unsaturated ester of formula As examples of protecting groups there may be mentioned acyl groups which are removable by any technique conventional in the art. These compounds of formula (XIV) can be easily prepared from the corresponding amines using standard techniques.

When M represents a group of formula $CH_2NH_2$, Q represents a nucleophilic group and G represents a hydrogen atom the compound of formula (V) can be represented by the formula (XV) (c.f. method (A) (b))

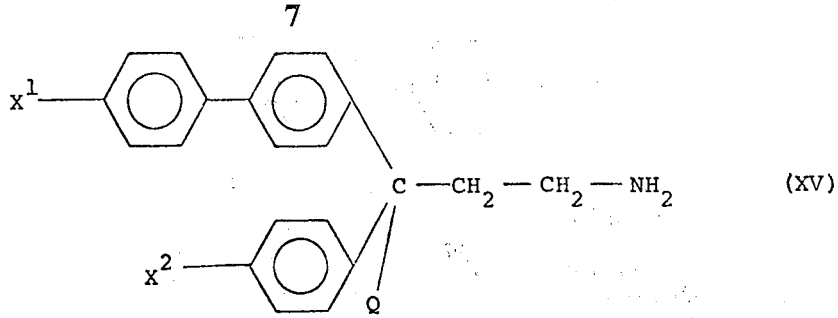 (XV)

In the above compound, it is preferred that Q be a hydroxyl group since the elements of water can be removed from such compounds simply by treatment with a strong acid such as concentrated hydrochloric acid in glacial acetic acid.

The preferred method of preparation of compounds of formula (XV) in which Q is a hydroxyl group is to react a ketone of formula (VII) with acetonitrile under anhydrous conditions in the presence of an alkali/metal amide, e.g. sodamide or an alkali metal hydroxide, e.g. potassium hydroxide to give the carbinol nitrile of formula

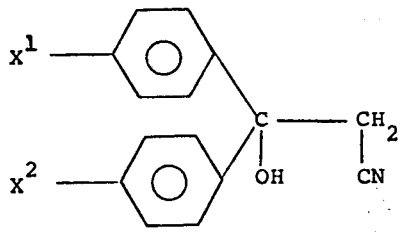

which is then reduced, for example, by a metallic hydride such as lithium aluminium hydride or by sodium in alcohol to the aminocarbinol of formula (XV) in which Q represents a hydroxyl group.

Compounds of formula (XV), where Q is a hydroxy group, can also be prepared (albeit with some difficulty) by the reaction of an organometallic reagent of formula

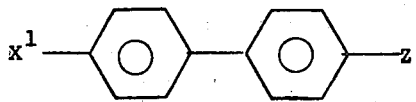

where $X^1$ is as defined previously and where Z is, for example, a magnesium halide or lithium, with a ketone of formula (XVII)

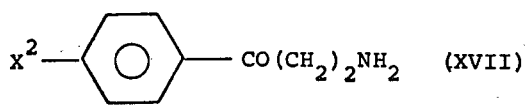

or by the reaction of an organometallic reagent of formula

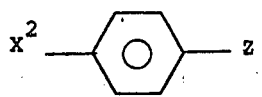

wherein $X^2$ and Z are as defined previously, with a ketone of formula (XVIII)

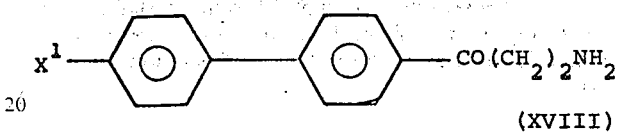

Compounds of formula (I) can also be prepared by a Wittig reaction between a phosphorane of formula

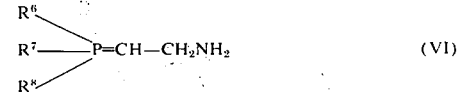 (VI)

and a ketone of formula

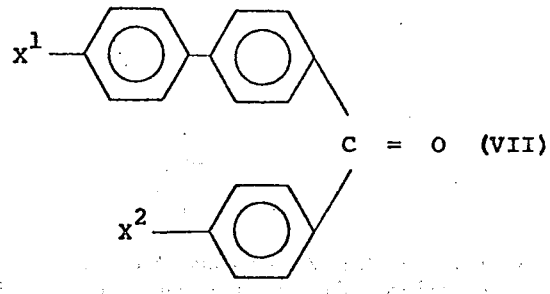

(c.f. method (B))

Standard Wittig reaction conditions known in the art can be used for this process. The phosphorane can be generated, in situ if desired, by the reaction of an appropriate phosphonium halide with a strong base, such as an organometallic compound, e.g. butyl lithium.

These ketones may be prepared by any suitable method, for example by a Friedel-Crafts reaction between an appropriately substituted biphenyl derivative and a benzoyl chloride or by a Friedel-Crafts reaction between an acid chloride of formula (XIX)

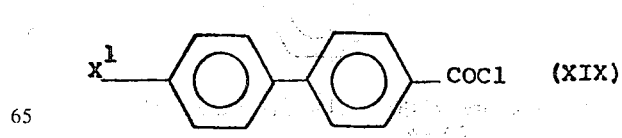

and an appropriately substituted benzene derivative.

Alternatively, they may be prepared by the halogenation, for example chlorination or bromination, of the 4-biphenylyl p-halogenophenyl ketone.

Compounds of formula (I), can also be prepared by the reduction of a compound of formula (VIII). (c.f. method (C))

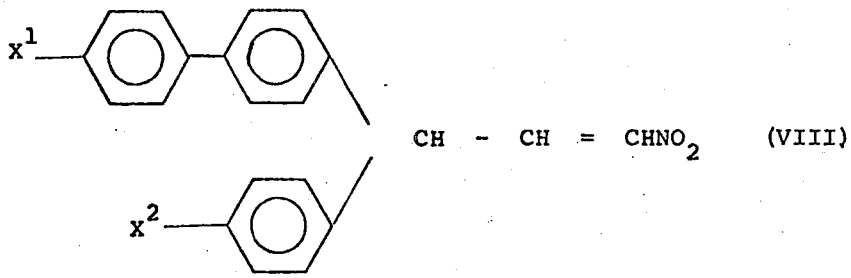

using, for example, hydrogen over platinum.

The compounds of formula (VIII) can be prepared from the aldehyde of formula (XXII)

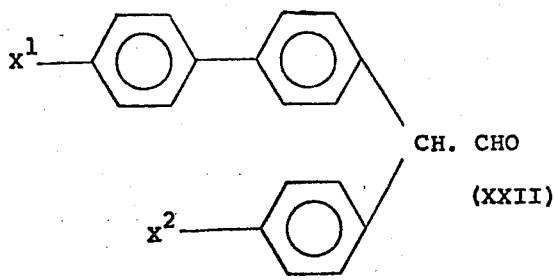

by condensation with nitromethane. This aldehyde of formula (XXII) can be prepared by the hydrolysis in aqueous sodium ethoxide, followed by acidification, of the epoxide of formula (XXIII)

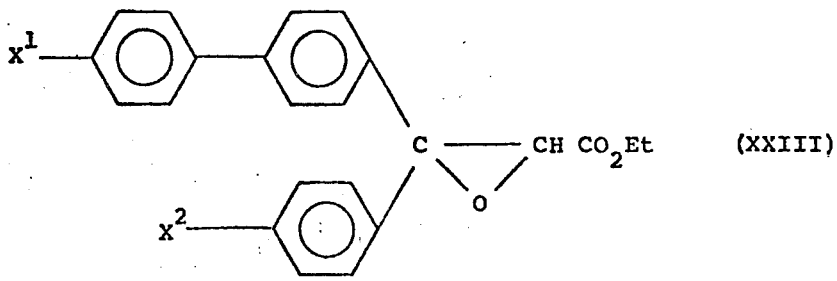

which can itself be prepared from the corresponding ketone of formula (VII) using ethylchloroacetate and sodamide.

The cis and trans isomers can be separated using, for example, fractional crystallisation of the bases, hydrochlorides acid maleates or oxalates. Alternatively, in some cases a base exchange resin may be used to effect the desired separation.

The preferred method of the present invention is that described in process (A) (b) where Q is a hydroxyl group.

The intermediates of formula (VI), are novel compounds and are therefore provided in a further aspect of the invention.

The present invention also provides a pharmaceutical formulation which comprises a substituted 3-amino-prop-1-ene of formula (I), or pharmaceutically acceptable salt thereof, and a pharmaceutically acceptable carrier therefor.

The preferred pharmaceutically acceptable salt is the hydrochloride.

In a further aspect of the invention there is provided a method of preparing a pharmaceutical formulation as defined above which comprises bringing into association the substituted 3-amino-prop-1-ene of formula (I), or pharmaceutically acceptable salt thereof and the pharmaceutically acceptable carrier therefor.

As stated above, the compounds of formula (I) may be presented in a pharmaceutical formulation for administration to a host infected with *T. cruzi*. They may be made by admixture of the components using any conventional technique used for making such formulations.

A compound of formula (I) may thus be presented in discrete units, such as tablets, capsules, cachets or ampoules each containing a predetermined quantity of the compound. These formulations may include one or more of the following carriers; solid diluents, flavouring, binding, dispersing, surface active, thickening, and coating materials and preservative, antioxidants and bacteriostats.

A preferred mode of presentation is a tablet which may be produced by granulating the active ingredient with a diluent and, preferably, a lubricant and compressing the granules into tablets. Formulations for subcutaneous administration are also another preferred mode of presentation and these may be made by presenting the compound as a sterile powder in a sealed container for dilution with sterile water.

For use in treating human infections of *T. cruzi*, it is estimated from data obtained from in vivo experiments with mice that doses which could be administered daily are of the order of 5 mg to 500 mg/kg, preferably 25 mg to 200 mg/kg, more preferably 50 mg to 100 mg/kg. For example, it is estimated that a dose of 50 mg/kg given daily for a month will prove effective against infections of *T. cruzi*.

Naturally, the dosage levels indicated above will be varied at the discretion of the physician according to the degree of infection and other attendant circumstances.

The invention will now be illustrated with reference to the following Examples.

EXAMPLE 1

1-(4'-chloro-4-biphenylyl)-1-p-chlorophenyl-3-aminoprop-1-ene and its cis isomer ($X^1 = Cl$; $X^2 = Cl$)

4'-Chloro-4-biphenylyl 4-chlorophenyl ketone (16.4 g.) and acetonitrile (2.25 g.) were reacted in benzene in the presence of sodamide (2.5 g.) by the method of Lettre and Wick (Annalen, 1957, 603, 194) to give 3-hydroxy-3-(4'-chloro-4-biphenylyl)-3-p-chlorophenylpropionitrile, m.p. 123°C after recrystallisation from benzene; λ max (ethanol) = 260 nm.

The nitrile was dissolved in a mixture of tetrahydrofuran (80 ml) and ether (80 ml) and added over 30 minutes at room temperature under nitrogen to a stirred suspension of lithium aluminium hydride (2.88 g.) in ether (75 ml). After stirring for a further hour the mixture was decomposed by addition of water (2.8 ml) and aqueous N sodium hydroxide (12 ml). After filtration, the organic layer was separated and evaporated to give 1-(4'-chloro-4-biphenylyl)-1-(4-chlorophenyl)-3-aminopropan-1-ol, m.p. 131°-2°C after recrystallisation from ethanol; λ max (ethanol) =261 nm.

The aminopropanol, dehydrated by boiling under reflux with glacial acetic acid (40 ml) and hydrochloric acid (10 ml) gave a mixture of cis- and trans-1-(4'-chloro-4-biphenylyl)-1-p-chlorophenyl-3-aminoprop-1-enes. The mixture was converted to hydrochlorides which were separated by fractional crystallisation from ethanol to give the sparingly soluble transisomer hydrochloride, m.p. 224°-226°C, λ max (ethanol) = 284 nm, isomeric purity by n.m.r., > 98%, and the more soluble cis-isomer hydrochloride, m.p. 214°-216°C, λ max (ethanol) = 260 nm, isomeric purity by n.m.r. > 98%.

In another experiment the mixture was converted to the acid maleate salts and the cis isomer acid maleate, which was crystallised from ethanol, had a m.p. of 175°.

EXAMPLE 2

1-(4'-bromo-4-biphenylyl)-1-p-chlorophenyl-3-aminoprop-1-ene and its cis isomer ($X^1 = Br$; $X^2 = Cl$)

4'-Bromo-4-biphenylyl-4-chlorophenyl ketone (74 g.), prepared by the reaction of p-chlorobenzoyl chloride and 4-bromobiphenyl in the presence of aluminium chloride, acetonitrile (12 g.) and sodamide (10 g.) were reacted in benzene by the method of Example 1 to give 3-hydroxy-3-(4'-bromo-4-biphenylyl)-3-p-chlorophenylpropionitrile, mp 160°-161°C after recrystallisation from benzene; λ max (ethanol) = 262 nm.

The nitrile was reduced with lithium aluminium hydride by the method of Example 1 to give 1-(4'-bromo-4-biphenylyl)-1-p-chlorophenyl-3-amino-propan-1-ol, mp 154°-155°C after recrystallisation from ethanol; λ max (ethanol) = 263 nm.

The aminopropanol, dehydrated by the method of Example 1 gave a mixture of cis- and trans-1-(4'-bromo-4-biphenylyl)-1-p-chlorophenyl-3-aminoprop-1-enes. The mixture was converted to hydrochloride which were separated by fractional crystallisation from ethanol to give the sparingly soluble trans-isomer hydrochloride, mp 240°C, λ max (ethanol) = 286 nm, isomeric purity by nmr > 98%, and the more soluble cis-isomer hydrochloride, mp. 235°-236°C, λ max (ethanol) = 262 nm, isomeric purity by nmr > 98%.

In another experiment the mixture was converted to the acid maleate salts and the cis isomer acid maleate, which was crystallised from ethanol, had a m.p. of 181°.

EXAMPLE 3

1-(4'-bromo-4-biphenylyl)-1-p-bromophenyl-3-aminoprop-1-ene and its cis isomer ($X^1 = Br$; $X^2 = Br$)

4'-Bromo-4-biphenylyl-4-bromophenyl ketone was reacted with acetonitrile by the method of Example 1 to give 3-hydroxy-3-(4'-bromo-4-biphenylyl)-3-p-bromophenylpropionitrile, mp. 154° after crystallisation from benzene; λ max (ethanol) = 261 nm. The nitrile was reduced with lithium aluminium hydride by the method of Example 1 to give 1-(4'-bromo-4-biphenylyl)-1-p-bromophenyl-3-aminopropan-1-ol, mp. 151° after recrystallisation from ethanol; λ max = 263 nm. The aminopropanol, dehydrated by boiling under reflux with glacial acetic acid and hydrochloric acid, gave a mixture of cis- and trans-1-(4'-bromo-4-biphenylyl)-1-p-bromophenyl-3-aminoprop-1-enes. The mixture was converted to the hydrochlorides which were separated by fractional crystallisation from ethanol into the more sparingly soluble trans-isomer hydrochloride, mp 246°, λ max (ethanol) = 286 nm, isomeric purity by n.m.r. > 98%, and the more soluble cis-isomer hydrochloride, mp 231°, λ max (ethanol) = 264 nm, isomeric purity by n.m.r. > 95%.

EXAMPLE 4

A tablet containing cis-1-(4'-chloro-4-biphenylyl)-1-p-chlorophenyl-3-aminoprop-1-ene was made up from the following components:

| | | |
|---|---|---|
| (i) | Cis-1-(4'-chloro-4-biphenylyl)-1-p-chlorophenyl-3-aminoprop-1-ene. | 250 mg |
| (ii) | Lactose B.P. | 125 mg |
| (iii) | Starch B.P. | 40 mg |
| (iv) | Methyl hydroxyethyl cellulose | 6 mg |
| (v) | Magnesium stearate B.P. | 2 mg |

Components (i) and (ii) were granulated and mixed together with a 5% solution of component (iv) in 50% aqueous alcohol. The granules were dried at 50% and components (iii) and (v) added. Mixing was then carried out, followed by compression into tablets.

EXAMPLE 5

A hard capsule containing cis-1-(4'-bromo-4-biphenylyl)-1-p-chlorophenyl-3-aminoprop-1-ene was formed from the following components:

| | | |
|---|---|---|
| (i) | Cis-1-(4'-bromo-4-biphenylyl)-1-p-chlorophenyl-3-aminoprop-1-ene. | 100 mg |
| (ii) | Talc B.P. | 10 mg |

-continued (iii) Starch B.P.     40 mg

Component (i) was ground up and then mixed with components (ii) and (iii). The mixed powder was used to fill hard gelatin capsules.

EXAMPLE 6

A tablet containing trans-1-(4'-bromo-4-biphenylyl)-1-p-bromophenyl-3-aminoprop-1-ene hydrochloride as the active ingredient was made up from the following ingredients:

| | | |
|---|---|---|
| (i) | Trans-1-(4'-bromo-4-biphenylyl)-3-aminoprop-1-ene hydrochloride | 500 mg |
| (ii) | Microcrystalline cellulose | 150 mg |
| (iii) | Starch B.P. | 50 mg |
| (iv) | Gelatin B.P. | 10 mg |
| (v) | Magnesium stearate B.P. | 2 mg |

Component (i) was granulated with half of components (ii) and (iii) with a 10% solution of component (iv) in 50% aqueous alcohol. The mixture was dried at 50°C. The remainder of components (ii) and (iii) and also component (v) were then added to the dried granules and mixing carried out. The mixture was then compressed into tablets.

EXAMPLE 7

A syrup was made up from the following ingredients:

| | | |
|---|---|---|
| (i) | Cis-1-(4'-bromo-4-biphenylyl)-1-p-bromophenyl-3-aminoprop-1-ene hydrochloride | 500 mg |
| (ii) | Sucrose B.P. | 30 g |
| (iii) | Glycerin B.P. | 15 g |
| (iv) | Methyl hydroxybenzoate B.P. | 0.1 g |
| (v) | Saccharin Sodium B.P. | 0.1 g |
| (vi) | Amaranth B.P.C. 1954 | 1.0 mg |
| (vii) | Purified water B.P. | to 100 ml |

Components (ii), (iv) and (v) were dissolved in purified water and components (iii) and (vi) then added. To this aqueous mixture was added component (i) which was dissolved therein. Sufficient purified water was then added to adjust the volume to 100 ml. After filtration the syrup was ready for use.

What we claim is:

1. A compound of formula (I),

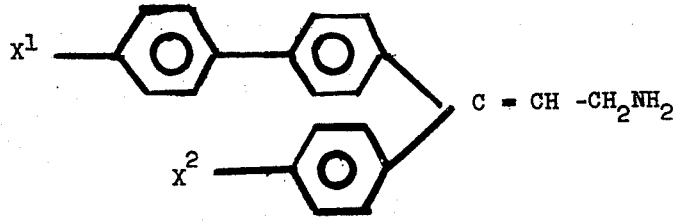

(I)

wherein $X^1$ and $X^2$ are the same or different and each is a halogen atom.

2. A pharmaceutically acceptable salt of the compound of claim 1.

3. The compound as defined in claim 1, wherein the para-halo biphenylyl and $CH_2NH_2$ groups are in a cis relationship.

4. A pharmaceutically acceptable salt of the compound of claim 3.

5. The hydrochloride or acid maleate salt of the compound of claim 3.

6. The hydrochloride salt of the compound of claim 3.

7. 1-(4'-chloro-4-biphenylyl)-1-p-chlorophenyl-3-aminoprop-1-ene.

8. A pharmaceutically acceptable salt of the compound of claim 7.

9. The hydrochloride salt of the compound of claim 7.

10. The compound of claim 7 wherein the para chloro-biphenylyl and $CH_2NH_2$ groups are in a cis relationship.

11. The hydrochloride or acid maleate salt of the compound of claim 10.

12. The hydrochloride salt of the compound of claim 10.

13. 1-(4'-bromo-4-biphenylyl)-1-p-chlorophenyl-3-aminoprop-1-ene.

14. A pharmaceutically acceptable salt of the compound of claim 13.

15. The hydrochloride salt of the compound of claim 13.

16. The compound of claim 13 wherein the para-bromo-biphenylyl and $CH_2NH_2$ groups are in a cis relationship.

17. The hydrochloride salt or acid maleate salt of the compound of claim 16.

18. The hydrochloride salt of the compound of claim 16.

19. 1-(4'-bromo-4-biphenylyl)-1-p-bromophenyl-3-aminoprop-1-ene.

20. A pharmaceutically acceptable salt of the compound of claim 19.

21. The hydrochloride salt of the compound of claim 19.

22. The compound of claim 19 wherein the para-bromo-biphenylyl and $CH_2NH_2$ groups are in a cis relationship.

23. The hydrochloride salt or acid maleate salt of the compound of claim 22.

24. The hydrochloride salt of the compound of claim 22.